(12) United States Patent
Okay

(10) Patent No.: US 6,521,215 B2
(45) Date of Patent: Feb. 18, 2003

(54) COMPOSITIONS AND METHODS FOR TOOTH TREATMENT

(76) Inventor: Devin Okay, 455 E. 86th St. Apt.# 27-B, New York, NY (US) 10028

(*) Notice: Subject to any disclaimer, the term of this patent is extended or adjusted under 35 U.S.C. 154(b) by 0 days.

(21) Appl. No.: 09/909,279

(22) Filed: Jul. 19, 2001

(65) Prior Publication Data

US 2002/0028251 A1 Mar. 7, 2002

Related U.S. Application Data

(63) Continuation-in-part of application No. 09/322,664, filed on May 28, 1999.

(51) Int. Cl.$^7$ .............................. A61K 7/16; A61K 7/20; A61K 7/28
(52) U.S. Cl. ............................. 424/50; 424/49; 424/53; 424/57; 433/215; 433/216
(58) Field of Search ..................................... 424/49–58

(56) References Cited

U.S. PATENT DOCUMENTS

| | | | | |
|---|---|---|---|---|
| 3,962,107 A | * | 6/1976 | Levin et al. ................. | 252/100 |
| 4,082,841 A | * | 4/1978 | Pader .......................... | 424/50 |
| 4,152,418 A | * | 5/1979 | Pader .......................... | 424/50 |
| 4,155,868 A | * | 5/1979 | Kaplan et al. ................. | 252/95 |
| 4,986,981 A | * | 1/1991 | Glace et al. ................... | 424/50 |
| 5,041,280 A | * | 8/1991 | Smigel ......................... | 424/53 |
| 5,171,564 A | * | 12/1992 | Nathoo et al. ................. | 424/53 |
| 5,256,402 A | * | 10/1993 | Prencipe et al. ............... | 424/53 |
| 5,279,816 A | * | 1/1994 | Church et al. ................. | 424/53 |
| 5,603,922 A | | 2/1997 | Winston et al. | |
| 5,605,675 A | | 2/1997 | Usen et al. | |
| 5,611,687 A | * | 3/1997 | Wagner ....................... | 433/80 |
| 5,614,175 A | | 3/1997 | Winston et al. | |
| 5,725,843 A | | 3/1998 | Fischer | |
| 5,746,598 A | | 5/1998 | Fischer | |
| 5,762,502 A | | 6/1998 | Bahn et al. | |
| 5,779,471 A | * | 7/1998 | Tseng et al. .................. | 433/80 |
| 5,851,574 A | * | 12/1998 | Hassan et al. ................ | 424/53 |
| 5,914,305 A | * | 6/1999 | Madison et al. ............. | 510/367 |
| 5,989,526 A | * | 11/1999 | Aaslyng et al. ............... | 424/50 |
| 6,120,754 A | * | 9/2000 | Lee et al. ...................... | 424/49 |
| 6,214,321 B1 | * | 4/2001 | Lee et al. ...................... | 424/52 |
| 6,331,291 B1 | * | 12/2001 | Glace et al. ................... | 424/49 |

FOREIGN PATENT DOCUMENTS

| | | | |
|---|---|---|---|
| GB | 2290233 | * | 12/1995 |
| WO | 95/17158 | * | 6/1995 |
| WO | 96/29978 | * | 10/1996 |
| WO | 97/06775 | * | 2/1997 |
| WO | 99/25315 | * | 5/1999 |

OTHER PUBLICATIONS

Denmat Homepage http://www.denmat.com/main.htm "Rembrandt" Product Line, 1998–1999.*

Ultradent Online http://www.ultradent.com 'Opalescence' Product Line, 1999.*

Discus Dental Homepage http://www.discusdental.com, 1999.*

Attin, T., Kielbassa, A.M., Schwanenberg, M., and Hellwig, E. Effect of fluoride treatment on remineralization of bleached enamel. J. Oral Rehabil. 24(4): 282–286, 1997 (Exhibit H).

Chow, L.C., Takagi S. Costantino, P.D., and Friedman, C.D. Self–setting calcium phsophate cements. In: Specialty Cements With Advanced Properties, B.E. Scheetz, A.G. Landers, I. Older, and H. Jennings, editors, Material Research Soc. Symp. Proc., vol. 179, pp. 3–24, 1991 (Exhibit I).

Ernst, C.P., Marroquin, B.B., and Willershausen–Zonnchen, B. Effects of hydrogen peroxide–containing bleaching agents on the morphology of human enamel. Quintessence Int. 27(1): 53–56, 1996 (Exhibit J).

Garber, D.A. Dentist–monitored bleaching: a discussion of combination and laser bleaching. J. Am. Dent. Assoc. 128 Suppl: 26S–30S, 1997 (Exhibit K).

Haywood, V.B. and Robinson, F.G. Vital tooth bleaching with Nightguard vital bleaching. Curr. Opin. Cosmet. Dent. 4: 45–52, 1997 (Exhibit L).

Lebedeva, G.K. and Galchenko, V.M. [Remineralization in combined combined treatment of fluorosis]. Stomatologiia (Mosk) 60(1): 21–22, 1981 [in Russian] (Exhibit M).

Lys–Masanes, I. and Goldberg, M. La méthode de blanchiment BV bleaching vital. Incidence des traitments chimiques sur l'email. [The V.B. vital bleaching method. Effect of chemical treatment on enamel]. Chir. Dent. Fr. 59(456): 39–41, 1989 [in French] (Exhibit N).

Lys–Masanes, I. and Goldberg, M. La methode de blanchiment B.V. bleaching vital: Reminéralisation en présence de fluorures. [The V.B. vital bleaching method: remineralization in the presence of fluorides]. Chir. Dent. Fr. 60(500–501) : 111–112, 1990 [in French] (Exhibit O).

McCracken, M.S. and Haywod, V.B. Demineralization effects of 10% carbamide peroxide, J. Dent. 24(6): 395–398, 1996 (Exhibit P).

Nathanson, D. Vital tooth bleaching: sensitivity and pulpal consideration. J. Am. Dent. Assoc. 128 Suppl: 41S–44S, 1997 (Exhibit Q).

Nathoo, S. The chemistry and mechanisms of extrinsic and intrinsic discoloration. J. Am. Dent. Assoc. 128 Suppl: 6S–10S, 1997, (Exhibit R).

Zhu, Q. [An approach to removing stains and remineralization of dental fluorosis]. Chung Hua Kou Chiang Hsueh Tsa Chih 26(4): 195–198, 253, 1991 [in Chinese] (Exhibit S).

* cited by examiner

Primary Examiner—Shep K. Rose
(74) Attorney, Agent, or Firm—Cooper & Dunham LLP

(57) ABSTRACT

The patent disclosure describes advantageous compositions and methods for whitening and remineralizing teeth, for desensitizing teeth, and for treating dental caries.

16 Claims, 1 Drawing Sheet

FIGURE 1A
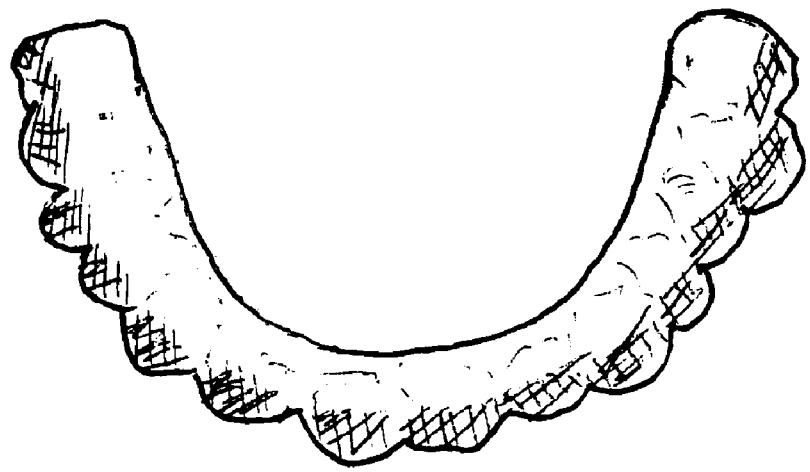
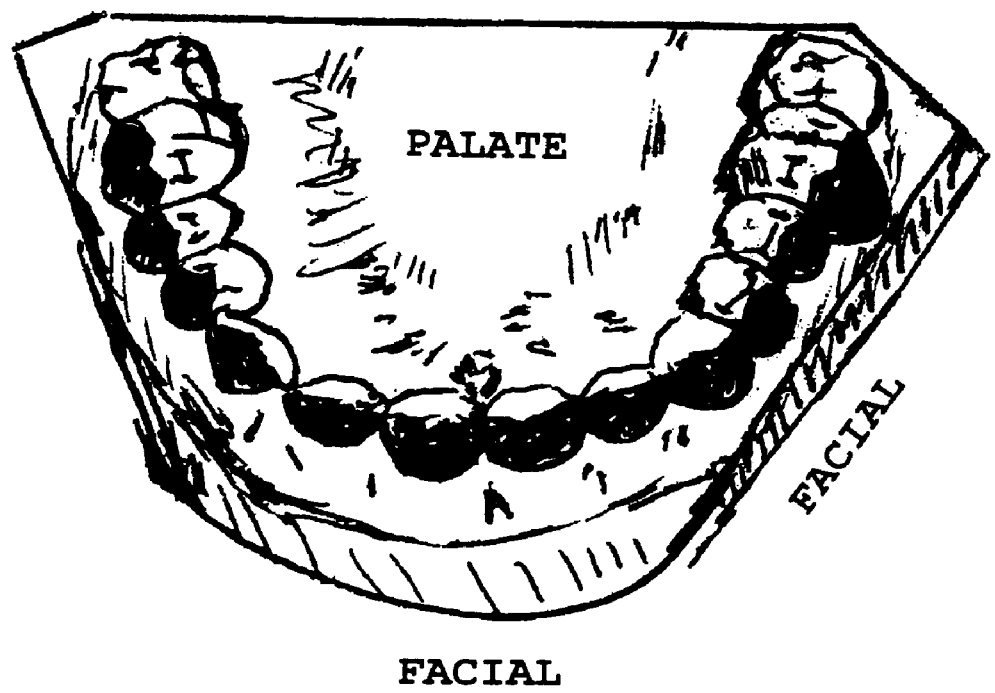
FIGURE 1B

COMPOSITIONS AND METHODS FOR TOOTH TREATMENT

This application is a continuation-in-part of U.S. Ser. No. 09/322,664, filed May 28, 1999, the contents of which are hereby incorporated by reference into the subject application.

BACKGROUND

Throughout this application, various publications are referenced in parentheses by author and year. Full citations for these references may be found at the end of the specification immediately preceding the claims. The disclosures of these publications in their entireties are hereby incorporated by reference into this application to describe more fully the art to which this patent specification pertains.

Whitening and remineralization of teeth are directed to the enamel and dentin of teeth, as the art is currently understood. A current understanding of factors relevant to whitening and remineralization is discussed below.

Dental enamel and dentin are primarily composed of calcium phosphate in the form of calcium hydroxyapatite. Enamel is the hardest tissue in the human body due largely to its degree of calcification. The mineral hydroxyapatite makes up approximately 95% of the total weight of enamel, compared with 70% of the total weight of dentin and 45% of the total weight of bone. A small amount of epithelial-produced enamel matrix is present in enamel, about 1% of its total weight. Water is responsible for the remaining 4%. Enamel prisms or rods are highly calcified structural units. The enamel prisms are separated from each other by thin noncalcified sheaths of enamel matrix, the prism sheaths. As a rule, the enamel prisms run almost perpendicular from the dentin-enamel junction to the enamel surface, across the entire width of the enamel. This means that the length of the prism depends on its location. It is 3–4 mm at cusps or incisal edges, whereas at the cervix or neck of the tooth it may be negligible in length. The average width of an enamel prism is 4 microns, but the width varies. It is wider at the surface of the tooth and becomes narrower near the dentin-enamel junction. The hydroxyapatite crystallites in enamel are unusual in that they are 4 times larger in all dimensions than the hydroxyapatite crystallites in dentin, cementum, and bone. There is a gradual change in orientation of the crystal from parallel to perpendicular, head to tail, in cross-section. The average width of a prism sheath is 0.1–0.2 microns and consists of remnant glycoproteins of the enamel matrix (amelogenins and enameling)

Protease enzymes play a role in the development of enamel (Robinson et al., 1997). During development, the extracellular protein matrix comprises distinct proteins: amelogenins (the dominant group of the secretory stage enamel matrix), proline-rich non-amelogenins (amelins, ameloblastins or prism sheath proteins, comprising 10% of developmental proteins), enzymes (proteases, alkaline phosphatase, and carbonic anhydrase), and extraneous serum proteins of which albumin is the most notable. Albumin is degraded by proteases as enamel maturation continues. Any proteins or peptides remaining could potentially inhibit final crystal growth. If, during enamel formation, the organism is under some stress (e.g., disease or birth), the enamel deposited at the time may show some irregularities in its calcification and disruption of the enamel prisms, producing incremental lines (Retzius). The lines are darker in ground section due to its larger amount of enamel matrix and to a lesser degree to its calcification. Near the cervix of the tooth large numbers of regularly spaced incremental lines may be found in enamel, suggesting that something other than disease may be involved in the production of those lines (Moss-Salentijn, 1985).

Protease has been used in dental treatment as part of an enzymatic process for conditioning dentin surfaces to improve bonding between restorative materials and teeth (Balm and Stewart, U.S. Pat. No. 5,762,502).

Stains on teeth can be of the extrinsic or intrinsic type. The types of attractive forces involved in extrinsic dental stains include electrostatic and van der Waal forces, hydration forces, hydrophobic interactions, dipole-dipole moment forces, and hydrogen bonds. The strength of adhesion for chromogens and pre-chromogens are not well understood. A method of classification was attempted to further describe dental stains which involves three categories (Nathoo, 1997).

In category 1 stains, the color of the discoloration is the same as the color of the material (chromogen) that causes the stain. The substances of tea, coffee and wine contain tannins and are composed of polyphenols such as catechins and leucoanthocyanins. These materials generate color due to the presence of conjugated double bonds and are thought to interact with the tooth surface via an ion exchange mechanism. Also included in the mechanism of adherence of the chromogen to the tooth is the salivary pellicle, a protein structure adhering to enamel via calcium bridges.

In category 2 stains, pigmented materials bind to the pellicle or tooth and subsequently change color. An example of this would be the cervical yellow stain turning brown with age. A proposed mechanism for this change is through the further accumulation or chemical modification of pellicle proteins (denaturation by acids or detergents). Intensification may occur via a metal bridging mechanism. Category 2 stains are considered to be more difficult to remove than category 1 stains.

In category 3 stains, the binding of a colorless material to teeth can undergo chemical reactions or transformations. The colorless material is termed a pre-chromogen. Examples of this type of staining are the induction of chlorhexidene stain, browning of foods high in carbohydrates and sugars via a rearrangement of the carbohydrates and amino acids, termed the Maillard or non-enzymatic browning reaction, and staining from stannous fluoride.

Thus, extrinsic stains result from chromogens binding either to enamel or probably more so to pellicle. The removal of a pellicle layer via a bleaching system will present a whiter tooth. The pellicle is a natural occurring biolayer and will re-establish itself if removed. It will do so with minimal chromogen build-up.

Intrinsic stains include phenomena occurring both before and after eruption of the tooth from the alveolar bone into the oral cavity. Pre-eruptive phenomena include endemic fluorosis, tetracycline staining, dentinogenesis imperfecta, and amelogenesis imperfecta. Post-eruptive phenomena include pulpal hemorrhaging, and deposition of secondary dentin or metals in a tooth from an amalgam restoration.

Various approaches to bleaching teeth have been proposed or used (e.g., Fischer, U.S. Pat. Nos. 5,725,843, 5,746,598). However, tooth bleaching does have side effects. The most common side effect is sensitivity and discomfort following treatment with a peroxide formulation. The incidence and severity of symptoms are dependent on the concentration of the peroxide formulation and dentine permeability. Although there may be no evidence of pulpal damage in humans, obliteration of odontoblasts, hemorrhage, inflammation and internal resorption of dentin were reported in dog tooth pulps (Seale et al., 1981). The differences in observed changes in humans can be explained by the average thickness and morphology of enamel and dentin. Patients who have large or poor restorations, cervical erosion, enamel cracks or similar problems require special attention. Fluoride treatment of eroded cervical areas, sealing of restoration, and premedication with an analgesic may prove helpful in treating patients with these findings (Nathanson, 1997).

Bleached enamel has demonstrated slight morphologic surface alterations under scanning electron microscopy (Ernst et al., 1996). Enamel microhardness is significantly decreased with a common bleaching agent, 10% carbamide peroxide (Opalescence®). High concentration fluoride application was found to restore hardness to enamel specimens (Attin et al., 1997). The amount of calcium lost from enamel exposed to 10% carbamide peroxide has been quantified via an atomic absorption spectrophotometer. Teeth exposed to carbamide peroxide lost an average of 1.06 micrograms/mm$^2$. This amount is small and may not be clinically significant (McCracken and Haywood, 1996).

Remineralization of teeth has been used when demineralization occurs naturally, for example in association with dental caries or dental hypersensitivity. In these procedures, remineralization has been achieved using either one-phase or two-phase compositions comprising calcium and phosphate, to which fluoride can be added (e.g., Usen and Winston, U.S. Pat. No. 5,605,675; Winston and Usen, U.S. Pat. Nos. 5,603,922, 5,614,175). Fluoride is known to enhance remineralization.

Because demineralization also occurs during tooth bleaching, efforts have been made to consider remineralization mechanisms. Saliva, or artificial saliva, can remineralize teeth after bleaching (Attin et al., 1997; Lys-Masanes and Goldberg, 1989; Zhu, 1991), and the effect can be enhanced by the addition of gluconate solution (Lebedeeva and Galchenk, 1981) or fluoride (Attin et al., 1997; Lys-Masanes and Goldberg, 1990). It has also been reported that bleached teeth can be recalcified using calcium phosphate solution (Zhu, 1991).

Commercial products for whitening teeth have been developed. These include Enamelon® "Calcium Whitening System" toothpaste, the ingredients of which include phosphoric acid, anhydrous dicalcium phosphate, sodium fluoride, and sodium gluconate (Enamelon, Inc., Cranbury, N.J.), and Rembrandt® "Low Abrasion Whitening Toothpaste," the ingredients of which include papain, dicalcium phosphate, and sodium monoflurophosphate (Den-Mat Corp., Santa Maria, Calif.).

The present application discloses advantageous compositions for whitening and remineralizing teeth, wherein the three key components are a whitening agent, a protease enzyme, and a remineralizing agent.

SUMMARY OF THE DISCLOSURE

Advantageous compositions for whitening and remineralizing teeth are disclosed, which comprise a whitening agent, a protease enzyme, and a remineralizing agent.

Advantageous kits and methods are disclosed for applying the whitening and remineralizing compositions described herein to teeth.

The compositions can be applied using different carriers which include, but are not limited to, a chewing gum, a toothpaste, a lozenge, a powder, a gel, a viscous gel, an ointment, a cream, a liquid, a mouthwash, and a candy.

The compositions, kits, and methods described herein can also be used to treat dental sensitivity and dental caries.

In alternative forms, the compositions, kits and methods described herein can be used in a dental office, at home, or in a veterinary setting.

BRIEF DESCRIPTION OF THE FIGURES

FIG. 1A. Polyethylene custom tray with facial surface relief, fabricated on a vacuform machine for use in applying protease-assisted bleaching and remineralization compositions to the teeth.

FIG. 1B. Gypsum study cast with added acrylic resin to facial surface.

DETAILED DESCRIPTION

An advantageous composition for whitening and remineralizing teeth is described in this patent disclosure. The composition comprises a whitening agent, a protease enzyme, and a remineralizing agent. In one embodiment, the composition consists essentially of a whitening agent, a protease enzyme, and a remineralizing agent.

A composition for whitening and remineralizing teeth in a subject's mouth is disclosed which comprises:

a) a protease enzyme, b) a whitening agent, wherein the whitening agent comprises greater than 10% peroxide, and c) a soluble calcium phosphate remineralizing agent.

In one embodiment, the composition consists essentially of:

a) a protease enzyme, b) a whitening agent, wherein the whitening agent comprises greater than 10% peroxide, and c) a soluble calcium phosphate remineralizing agent.

In different embodiments, the whitening agent is selected from the group consisting of one or more of carbamide peroxide and hydrogen peroxide. In one embodiment, the concentration of carbamide peroxide is between 11–20% by weight. In one embodiment, the concentration of hydrogen peroxide is between 30–50% by volume.

Different protease enzymes can be used can be used in the composition. Examples of proteases include, but are not limited to, the group consisting of one or more of papain, trypsin, chymotrypsin, aminopeptidase, carboxypeptidase, pepsin, and cathepsin. In a preferred embodiment, papain is used. In one embodiment, the protease enzyme is obtained from a papaya extract. In different embodiments, the concentration of protease can be between about 0.01 mg/ml to about 50 mg/ml. In one embodiment, the protease enzyme is between 40–85 units/mg of papain.

In different embodiments, the soluble calcium phosphate remineralizing agent is selected from the group consisting of one or more of monocalcium phosphate, dicalcium phosphate anhydrous, tricalcium phosphate, and tetracalcium phosphate. Dicalcium phosphate anhydrous and tetracalcium phosphate are preferred. In one embodiment, the concentration of calcium phosphate is between about 0.05% and about 20% by weight. In a preferred embodiment, the composition further comprises glycerin. In order for calcium phosphate to act as a remineralizing agent, it is essential that the calcium phosphate be in soluble form. If the calcium phosphate were to precipitate out of solution, it would function as an abrasive agent and not as a remineralizer. The addition of glycerin to the composition acts to prevent the calcium phosphate from forming a precipitate. In a different embodiments, the concentration of glycerin is between about 10–60% by weight.

In one embodiment, the composition further comprises fluoride, for example sodium fluoride. In one embodiment, the concentration of sodium fluoride is between about 0.01–5%.

In one embodiment, the remineralizing agent is white in color. Thus, the uptake of remineralizing material may contribute to the whitening effect.

In one embodiment, the composition contains potassium nitrate, which can act as a desensitizing agent.

The composition can be provided in a carrier. In different embodiments, the carrier is selected from the group consisting of a chewing gum, a toothpaste, a lozenge, a powder, a gel, a viscous gel, an ointment, a cream, a liquid, a mouthwash, and a candy.

The composition can be provided in an application kit for whitening and remineralizing teeth which comprises the composition and an apparatus for applying the composition to the subject's teeth. In one embodiment, the apparatus for applying the composition to the subject's teeth comprises a tray having a relief of a facial surface of a subject's teeth for applying said composition to the teeth when the tray is seated in the subject's mouth. Dental trays or dams can be used as a part of the system for applying the compositions described herein to the teeth (FIG. 1; e.g., Haywood and Robinson, 1997; Silverman, U.S. Pat. No. 5,165,424). In different embodiments, the kit is adapted for use in a home, a dental office, or a veterinary setting.

In a dental office setting, preferred embodiments of the whitening agent are 30–50% hydrogen peroxide; whereas for use in a home setting, 10–20% carbamide peroxide is preferred. An example of a preferred embodiment of the composition for use in a dental office setting includes 50% hydrogen peroxide, 50 mg/ml papain, and 20% tetracalcium phosphate.

The advantages of the compositions disclosed herein include possible synergistic effects between the actions of the protease and the whitening agent, and ease of use especially in a home or veterinary setting. The compositions described in this patent disclosure are believed to provide improved effects both on extrinsic dental stains and on previously "untouchable" intrinsic dental stains. The removal of chromogen from enamel is believed to be aided by the presence in the composition of a protease enzyme able to react with protein chromogens and the pellicle layer, creating enhanced mechanisms for penetration of an oxygen free radical bleaching agent (e.g., hydrogen peroxide molecule from carbamide peroxide solution or hydrogen peroxide solution). It is believed that one of the effects of including proteases with whitening agents in accordance with this patent disclosure is deeper penetration of the whitening agents into enamel, in addition to the beneficial effect of the reaction of proteases with protein chromogens.

The composition provides an advantageous ease of use in that it allows a whitening agent, a protease enzyme, and a remineralizing agent to be applied to teeth using only a single composition rather than having to apply the different components in separate compositions. This is particularly advantageous for home and veterinary use, and when the composition is supplied in certain carriers, such as for example chewing gum, toothpaste, lozenge, mouthwash, and candy.

The composition has the further advantage that when available application time is limited, the whitening agent, protease enzyme, and remineralizing agent are simultaneously applied to the teeth for the full duration of the application time. In contrast, for the same total available treatment time, if the whitening agent, protease enzyme, and remineralizing agent were applied in separate compositions, the time of application of each component would have to be reduced in order to keep total treatment time constant.

The teeth whitening and remineralizing composition preferably has the consistency of a viscous liquid or gel. In one embodiment of the composition, silica is added to the composition to increase the viscosity of the composition. In other embodiments, the composition contains methylcellulose (10–20%) or xantahan gum (10–20%).

In different embodiments, a sweetener or flavorant can be added to the composition. In one embodiment, the concentration is between about 0.2–10% by weight. In one embodiment the sweetener is saccharin or aspartame.

The pH of the composition can be adjusted. In a preferred embodiment, the pH is between about pH 6 to 7.5. In one embodiment, baking soda is used as a pH neutralizer.

Advantageous methods for whitening and remineralizing teeth are also disclosed. The methods comprise applying to teeth any of the compositions described herein for whitening and remineralizing teeth.

In a further embodiment of any of the methods of whitening and remineralizing a subject's teeth described herein, a gel polymer is used at the base of the teeth to contain the whitening and remineralizing compositions to the teeth and to avoid their contact with the gum. In different embodiments, the gel comprises polyethyl methylacrylate or polymethyl methylacrylate with plasticizers. A dental tray or dam can also be used for isolation of the dentition.

In a further embodiment of the methods of whitening and remineralizing teeth described herein, laser light is applied to teeth coated with the composition for whitening and remineralizing teeth. The penetration into the tooth of an oxygen free radical bleaching agent (e.g., hydrogen peroxide molecule from carbamide peroxide solution or hydrogen peroxide solution) is believed to be aided by the use of laser light, which can be absorbed within water containing substances of 0.10 mm (Garber, 1997). In different embodiments, the laser can be a $CO_2$ laser, a hydrogen fluoride laser, or an argon laser. The preferred embodiment uses a $CO_2$ laser. In an alternative embodiment, concentrated visible light is used. This procedure can be carried out in a dental office, particularly if it involves the use of a laser or concentrated visible light, or it can be adapted for home use.

The total time for application of whitening and remineralization compositions can typically vary from 20–30 minutes to 2–3 hours. In a home application setting, compositions can be applied to the teeth overnight. In home application kits, the treatment time may vary between 1–2 weeks to up to several weeks depending upon the stain. In one embodiment, the whitening and remineralizing composition includes a light activated, photo-initiator as an indicator of time exposure.

The compositions, kits and methods described herein can be used both on natural teeth and on artificial teeth.

Using the compositions, kits and methods described herein, the loss of calcium that may occur during dental bleaching can be restored by remineralization so that a more efficacious whitening composition can be used safely with enhanced effect.

Advantageous methods for treating dental sensitivity and for treating dental caries are also described in this patent disclosure which comprise applying any of the compositions described herein to the subject's teeth. Bleaching can cause dental sensitivity. This sensitivity can be treated using the described compositions, kits and methods for tooth whitening and remineralization. In addition, the described compositions, kits, and methods can be used to treat dental sensitivity that occurs in the absence of bleaching. Remineralization may decrease sensitivity by decreasing the permeability of dentin. In addition, the described compositions, kits and methods for tooth whitening and remineralization can be used in other applications where remineralization would be beneficial, for example in the treatment of dental caries.

After the whitening and remineralizing procedures described herein have been carried out, additional compositions for restorative or cosmetic purposes may be applied to the teeth.

EXPERIMENTAL DETAILS

Protease Enhanced Tooth Whitening

Protease application on human teeth specimens demonstrated both a whitening effect of protease on the enamel surface and a protease-induced enhancement of the whitening effect of hydrogen peroxide. In this experiment, specimens were prepared in vitro by dividing the enamel surface of the teeth into left and right halves with a visible light cured polymer. This allowed a shade comparison of one side to the other. Specimens were divided into two groups. In both groups, one side of the teeth received an application of protease. Protease slurry was prepared by mixing papain (papaya, crude, Type III) with distilled water and applied via a syringe tip applicator. One group of specimens was then immersed in 30% hydrogen peroxide solution. The other group received no further treatment. Thus, in the first group, one-half of the tooth was first treated with papain and then with hydrogen peroxide, and the second half of the tooth was treated with only hydrogen peroxide. In the other group, one-half of the tooth was treated with papain and the second half of the tooth was untreated.

The results showed a distinct change in the shade of sides treated with a protease in both groups. The experiment demonstrates that protease application alone will remove stains and "whiten" a tooth. Furthermore, when protease is used with a subsequent application of hydrogen peroxide solution more efficacious whitening is produced than when hydrogen peroxide is used alone. A scanning electron microscope (5000× magnification) was used to compare an untreated tooth surface, a surface treated with hydrogen peroxide alone, and a surface treated with both protease and hydrogen peroxide. The enamel surface treated with protease and hydrogen peroxide demonstrated a microscopic "pitting" of the enamel not seen on the other surfaces. This perhaps demonstrates the removal of protein off the enamel surface leaving the ends of the enamel rods in view. Furthermore, it demonstrates an enamel surface amenable to remineralization following treatments that produce more efficacious whitening of the tooth.

Thus, the whitening and remineralizing system and method described in this disclosure provide three ways by which teeth may be whitened. First, protease itself has a whitening effect. Second, bleaching causes whitening of the teeth. This effect is enhanced by treatment with protease. Third, the uptake of the remineralization composition, which is white, may contribute to the whitening of the teeth.

Calcium Phosphate Remineralization Decreases Dentin Permeability

Experiments conducted in vitro with human teeth showed that a calcium phosphate compound applied to the dentin surface will decrease the permeability of the dentin. This result would explain why a calcium phosphate compound would decrease sensitivity at the cervix or root of the tooth, where the enamel is thinner or absent.

REFERENCES

Attin, T., Kielbassa, A. M., Schwanenberg, M., and Hellwig, E. Effect of fluoride treatment on remineralization of bleached enamel. J. Oral Rehabil. 24(4): 282–286, 1997.

Bahn, A. N. and Stewart, G. P. Process for adhering composites to human teeth. U.S. Pat. No. 5,762,502, Jun. 9, 1998.

Ernst, C. P., Marroquin, B. B., and Willershausen-Zonnchen, B. Effects of hydrogen peroxide-containing bleaching agents on the morphology of human enamel. Quintessence Int. 27(1): 53–56, 1996.

Fischer, D. E. Methods for bleaching teeth surfaces. U.S. Pat. No. 5,725,843, Mar. 10, 1998.

Fischer, D. E. Dental bleaching compositions including a sticky matrix material. U.S. Pat. No. 5,746,598, May 5, 1998.

Garber, D. A. Dentist-monitored bleaching: a discussion of combination and laser bleaching. J. Am. Dent. Assoc. 128 Suppl: 26S–30S, 1997.

Haywood, V. B. and Robinson, F. G. Vital tooth bleaching with Nightguard vital bleaching. Curr. Opin. Cosmet. Dent. 4: 45–52, 1997.

Lebedeva, G. K. and Galchenko, V. M. [Remineralization in combined treatment of fluorosis]. Stomatologiia (Mosk) 60(1): 21–22, 1981 [in Russian].

Lys-Masanes, I. and Goldberg, M. La méthode de blanchiment B. V. bleaching vital. Incidence des traitments chimiques sur l'email. [The V. B. vital bleaching method. Effect of chemical treatment on enamel]. Chir. Dent. Fr. 59(456): 39–41, 1989 [in French].

Lys-Masanes, I. and Goldberg, M. La methode de blanchiment B. V. bleaching vital: Reminéralisation en présence de fluorures. [The V. B. vital bleaching method: remineralization in the presence of fluorides] . Chir. Dent. Fr. 60(500–501): 111–112, 1990 [in French].

McCracken, M. S. and Haywood, V. B. Demineralization effects of 10% carbamide peroxide. J. Dent. 24(6): 395398, 1996.

Moss-Salentijn, L., Dental and Oral Tissues, Lea & Febiger, Philadelphia Pa., 1985.

Nathanson, D. Vital tooth bleaching: sensitivity and pulpal consideration. J. Am. Dent. Assoc. 128 Suppl: 41S–44S, 1997.

Nathoo, S. The chemistry and mechanisms of extrinsic and intrinsic discoloration. J. Am. Dent. Assoc. 128 Suppl: 6S–10S, 1997.

Robinson, C., Brookes, S. J., Bonass, W. A., Shore, R. C., Kirkham, J. Enamel maturation, Dental Enamel Ciba Foundation Symposium 205: 156–170, discussion 170–174, 1997.

Seale, N. S., McIntosh, J. E., and Taylor, A. N. Pulpal reaction to bleaching teeth in dogs. J. Dent. Res. 60: 948–953, 1981.

Silverman, H. N. Method and system for whitening teeth. U.S. Pat. No. 5,165,424, Nov. 24, 1992.

Usen, N. and Winston, A. E. Processes and compositions for remineralization and prevention of demineralization of dental enamel. U.S. Pat. No. 5,605,675, Feb. 25, 1997.

Winston, A. E. and Usen, N. Processes and compositions for the remineralization of teeth. U.S. Pat. No. 5,603,922, Feb. 18, 1997.

Winston, A. E. and Usen, N. Stable single-part compositions and the use thereof for remineralization of lesions in teeth. U.S. Pat. No. 5,614,175, Mar. 25, 1997.

Zhu, Q. [An approach to removing stains and remineralization of dental fluorosis]. Chung Hua Kou Chiang Hsueh Tsa Chih 26(4): 195–198, 253, 1991 [in Chinese].

What is claimed is:

1. A method of whitening and remineralizing teeth in a subject's mouth which consists essentially of applying a single composition to the subject's teeth, wherein the composition comprises:
   a) a protease enzyme;
   b) a whitening agent selected from the group consisting of one or more of carbamide peroxide and hydrogen peroxide, wherein the whitening agent comprises greater than 10% peroxide; and
   c) a soluble calcium phosphate remineralizing agent selected from the group consisting of one or more of monocalcium phosphate, tricalcium phosphate, and tetracalcium phosphate.

2. The method of claim 1, wherein the composition consists essentially of:
   a) a protease enzyme;
   b) a whitening agent selected from the group consisting of one or more of carbamide peroxide and hydrogen peroxide, wherein the whitening agent comprises greater than 10% peroxide; and
   c) a soluble calcium phosphate remineralizing agent selected from the group consisting of one or more of monocalcium phosphate, tricalcium phosphate, and tetracalcium phosphate.

3. The method of claim 1, wherein the concentration of carbamide peroxide is between 11–20% by weight.

4. The method of claim 1, wherein the concentration of hydrogen peroxide is between 30–50% by volume.

5. The method of claim 1, wherein the protease enzyme is selected from the group consisting of one or more of papain, trypsin, chymotrypsin, aminopeptidase, carboxypeptidase, pepsin, and cathepsin.

6. The method of claim 1, wherein the concentration of protease enzyme is between 0.01 mg/ml to 50 mg/ml.

7. The method of claim 1, wherein the protease enzyme is between 40–85 units/mg of papain.

8. The method of claim 1, wherein the concentration of calcium phosphate is between about 0.05% and about 20% by weight.

9. The method of claim 1, wherein the composition further comprises glycerin.

10. The method of claim 1, wherein the composition further comprises fluoride.

11. The method of claim 1, wherein the remineralizing agent is white in color.

12. The method of claim 1, which further comprises applying the composition to a dental tray and seating the dental tray in the subject's mouth so as to apply the composition to the subject's teeth.

13. The method of claim 1, wherein the subject is a human.

14. The method of claim 1, wherein the subject is a non-human animal.

15. The method of claim 1, wherein the composition reduces dental sensitivity of the subject.

16. The method of claim 1, wherein the composition treats dental caries of the subject.

* * * * *